(12) United States Patent
Armor et al.

(10) Patent No.: US 6,399,830 B1
(45) Date of Patent: Jun. 4, 2002

(54) SELECTIVE REDUCTIVE AMINATION OF NITRILES

(75) Inventors: John Nelson Armor, Orefield; Michael Edward Ford, Coopersburg; William Eamon Carroll, Orefield, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/735,587

(22) Filed: Dec. 13, 2000

(51) Int. Cl.$^7$ ............................................. C07C 209/48
(52) U.S. Cl. ...................... 564/490; 564/491; 564/492; 564/493
(58) Field of Search ................................ 564/490, 491, 564/492, 493

(56) References Cited

U.S. PATENT DOCUMENTS

| | | | |
|---|---|---|---|
| 5,557,011 A | 9/1996 | Witzel et al. ................. | 564/492 |
| 5,648,545 A | 7/1997 | Reif et al. .................... | 564/470 |
| 5,847,220 A | 12/1998 | Lassila ....................... | 564/493 |
| 5,869,653 A | 2/1999 | Johnson ....................... | 540/531 |
| 5,894,074 A | 4/1999 | Fuchs et al. ................. | 564/490 |

FOREIGN PATENT DOCUMENTS

CA     834244     2/1970

OTHER PUBLICATIONS

Database CAPLUS on STN, Acc. No. 1994:557131, Maeno et al., 'Preparation of long–chain aliphatic group–containing tertiary aliphatic amines.' JP 06072969 (abstract).*

Database CAPLUS on STN, Acc. No. 1994:191059, Barrault et al., 'One step synthesis of dissymetrical amines R2NR1 from nitriles in the presence of copper catalysts.' Stud. Surf. Sci. Catal. (1993), 78(Hetero. Cat. and Fine Chem. III), pp. 305–312 (abstract).*

* cited by examiner

Primary Examiner—Brian J. Davis
(74) Attorney, Agent, or Firm—Mary E. Bongiorno

(57) ABSTRACT

This invention pertains to an improvement in a process for the formation of secondary or tertiary amines by the catalytic reductive amination of a nitrile with a primary amine. The catalyst employed in the improved reductive amination process is one that has been promoted with an acidic promoter preferably a solid phase acidic promoter.

18 Claims, No Drawings

SELECTIVE REDUCTIVE AMINATION OF NITRILES

BACKGROUND OF THE INVENTION

Processes for the production of amines by the catalytic reductive coupling of a primary or secondary amine with a nitrile are known and widely used to produce a variety of secondary and tertiary amines. Di(fattyalkyl)alkylamines, and particularly di(fattyalkyl)methylamines, are representative of tertiary amines produced by reductive amination and are of particular value for the production of fabric softeners, hair conditioners, and antistatic agents.

Di(fattyalkyl)alkylamines can be converted to the fabric softeners, etc. via derivatization to the quaternary salt. Tertiary amine functionality is necessary for successful production of these derivatives. In contrast, intermediate mono(fattyalkyl)methylamines and byproduct secondary di(fattyalkyl)amines do not form the desired quaternary salts selectively, and therefore, are unsuited for processing to the desired end product. In addition, the intermediate and the byproduct amine lack the optimum balance of nonpolar (two long chain fattyalkyl groups) and polar (methylamino group) functionality to provide for the production of effective surfactants and antistats.

Representative patents which describe the reductive coupling of nitriles with amines are as follows:

U.S. Pat. No. 5,648,545 discloses the catalytic amination of a wide variety of nitriles by reacting a nitrogen compound such as ammonia, or a primary or secondary amine with the nitrile at temperatures of from about 80 to 250° C. and a hydrogen pressure of 1 to 400 bar. The catalytic amination is carried out in the presence of hydrogen and the catalyst is comprised of a reduced copper oxide/zirconium oxide. Alkali metal carbonate is added to the catalyst prior to reaction. An exemplary nitrile includes N-methylaminopropionitrile and representative amines reacted therewith includes mono and dimethylamine.

Canadian Patent 834,244 discloses a process for continuously producing high molecular weight secondary and tertiary amines by reacting high molecular aliphatic nitriles with volatile primary or secondary amines. The fatty acid nitriles have a carbon content from 8 to 22 carbon atoms and include lauryl and stearyl nitrile and the low boiling amines include dimethylamine, diethylamine, etc. The catalyst is an alkali-modified copper-chromium catalyst with the alkylation being conducted at a temperature of 120 to 180° C. and 180 to 210 atmospheres hydrogen pressure. Salts of alkali metals used in preparing the alkali-modified catalysts included those of potassium and sodium.

U.S. Pat. No. 5,869,653 discloses a process for the hydrogenation of nitriles to produce primary amines. In the catalytic hydrogenation of aliphatic nitriles, the nitrile is contacted with hydrogen in the presence of a sponge or Raney® cobalt catalyst employing lithium hydroxide as a promoter. A wide variety o f aliphatic nitriles ($C_{2-30}$) are suggested as being suited for conversion to the primary amine by reaction with hydrogen.

U.S. Pat. No. 5,847,220 discloses a process for the catalytic hydrogenation of a cyanopropionaldehyde alkyl acetal in the presence of a nickel or cobalt catalyst promoted with alkali metal hydroxide to form aminobutyraldehyde alkyl acetals, i.e., the primary amine derivative of the cyanoalkyl acetals. The background in the patent discloses a variety of processes for the hydrogenation of nitriles, but these processes generally deal with the hydrogenation of the nitrile itself, rather than a reductive alkylation by the reaction of the nitrile with a primary or secondary amine.

U.S. Pat. No. 5,557,011 discloses a process for producing diamines by reductive coupling of secondary amine with an aliphatic nitrile. In the background of the art, palladium/carbon catalysts were used as the primary reductive coupling catalyst. The improvement in the process wherein palladium is used as a catalyst resided in utilizing an oxidic support, such as a gamma alumina, silica, titania, zirconia, etc. which may be modified by inclusion of up to 15 wt % metal oxides of subgroups IB–VIIB, or Group VIII of the periodic table. Preparation of di-tert-amines from the corresponding dinitriles and secondary amines with palladium supported on an oxide (specifically, on an oxide selected from the group consisting of γ-alumina, silica, titania, or zirconia) or on an oxide treated with an alkali metal/alkaline earth oxide is shown.

U.S. Pat. No. 5,894,074 discloses a process for the preparation of tertiary amines from nitriles and secondary amines utilizing a palladium catalyst. The improvement in the process utilizing palladium as a catalyst or catalysts incorporating small amounts of calcium oxide, alumina, magnesium oxide, etc., resided in the inclusion of a small amount at least one further metal selected from the group of 1B and Group VIII, as well as cerium and lanthanum on a support. Examples of the latter class of catalysts include 0.5 wt % palladium/alumina with 20% calcium oxide and 1.0 wt % palladium/alumina with 20% magnesium oxide.

BRIEF SUMMARY OF THE INVENTION

This invention pertains to an improvement in a process for the formation of di(fattyalkyl)alkylamines, and particularly, di(fattyalkyl)methylamines, wherein a fatty nitrile is reacted with a primary alkylamine in the presence of a heterogenous metal reductive amination catalyst and hydrogen. The improvement resides in effecting the reaction in the presence of an effective amount of an acidic promoter, preferably a solid acidic promoter having a pK of less than or equal to about 2.

There are numerous advantages associated with the improved process and these include:

- an ability to produce di(fattyalkyl)alkylamines in high selectivity and at high production rates;
- an ability to produce di(fattyalkyl)alkylamines in a single step;
- an ability to produce a reaction product having a minor portion of byproduct mono(fattyalkyl)alkylamine thereby facilitating separation of the product di(fattyalkyl)alkylamine, from the mono(fattyalkyl)alkylamine;
- an ability to effect reductive coupling of two equivalents of a fatty nitrile with a primary amine to produce the corresponding mixed tertiary amine and minimize or avoid coproduction of the corresponding fatty di/trialkylamines;
- an ability to reductively aminate a wide range of nitriles; and,
- an ability to use the catalyst over an extended time.

DETAILED DESCRIPTION OF THE INVENTION

This invention pertains to a selective single step process for the reductive amination of nitriles to produce tertiary amines, especially fatty ($\leq C8$) nitriles, by reaction of the corresponding nitrile with a primary amine. This process chemistry comprises reacting two moles of a fatty nitrile with a primary amine through the intermediacy of the mono(fattyalkyl)methylamine followed by in situ reductive coupling with another mole of fatty nitrile to produce the di(fattyalkyl)methylamine.

The single step catalytic reductive amination is described in Equation 1.

(1)

Selectivity problems can occur in the above reaction. It is believed that selectivity to the di(fattyalkyl)alkylamines often suffers because of (a) failure to effect a second reductive coupling with the reductively coupled methylamine or (b) generation of an alternate byproduct. The alternate byproduct is believed to be formed owing to a competing reaction pathway: (a) reduction of the nitrile to the corresponding primary amine, and (b) subsequent coupling of that amine with a second equivalent of nitrile to generate a secondary di(alkyl)amine. The perceived pathway to this alternate byproduct is described by Equation 2.

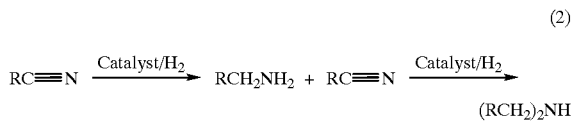
(2)

The objective is to minimize alternate byproduct formation set forth by equation 2.

In the practice of the process, a wide variety of nitriles may be used in the reductive amination process, and these nitriles include $C_{2+30}$ aliphatic and aromatic nitriles. Specific examples of nitriles include:

aliphatic nitriles such as acetonitrile, propionitrile, butyronitrile and valeronitrile; ether nitriles such as ethoxypropionitrile, methoxypropionitrile, isopropoxynitrile, biscyanoethylether, bis-(2-cyanoethyl)ethyleneglycol, bis-(2-cyanoethyl)diethyleneglycol, mono-(2-cyanoethyl)diethyleneglycol, bis(2-cyanoethyl)tetramethylene glycol; fatty nitriles, preferably $C_{8-20}$ fattyalkyl nitriles, saturated and unsaturated, e.g., lauronitrile, cocoalkyl nitrile, oleonitrile, tall oil fatty acid nitrile and stearonitrile; dinitriles such as adiponitrile, methylglutaronitrile and succinonitrile;

βaminonitriles formed by the reaction of acrylonitrile with $C_{1-30}$ alkylamines and $C_{1-8}$ alkanolamines such as β-aminopropionitrile, di-(2-cyanoethyl)amine, N-methyl-β-aminopropionitrile, N,N-dimethyl-β-aminopropionitrile, N-(2-cyanoethyl)ethanolamine, N,N-di-(2-cyanoethyl)ethanolamine, N-(2-cyanoethyl)diethanolamine and N-(2-cyanoethyl)propanolamine;

β-cyanoethylated amides such as those represented cyanoethylated acetamide and cyanoethylated propionamide; and, aromatic nitriles which may be used in the process include: benzyl cyanide, benzonitrile, isophthalonitrile and terephthalonitrile.

However, the preferred nitriles are the fatty nitriles having from 8–18 carbon atoms.

A wide variety of primary amines may be used in the reductive amination process. Representative amines which can be used in the reductive amination process are represented by the formula R'NH$_2$ where R' is lower alkyl having from ($C_1$ to $C_8$) carbons or aryl. Examples of candidate amines include primary amines such as monomethylamine, monoethylamine, monopropylamine, diamines such as ethylenediamine, propylenediamine, N-ethylethylenediamine, alkanolamines such as, ethanolamine, ether amines such as methoxypropylamine, methoxyethylamine, ethoxyethylamine, aryl amines such benzyl amine and cycloaliphatic amines such as cyclohexylamine. Preferred amines are the primary $C_{1-4}$ alkylamines, specifically methyl and ethyl amine.

Palladium is the heterogenous reductive amination catalytic metal of choice for the reductive amination reaction. Typically, the reductive amination catalyst is carried upon a heterogeneous support for ease of removal from the reaction medium. Representative supports include carbon, alumina, silica, kielsulghur, and the like. The heterogeneous catalytic metal component, palladium, is carried on the support in an amount usually ranging from about 2 to 20% by weight and preferably from 3–10% and most preferably from 4 to 6% by weight. Other metals such as ruthenium, rhodium, cyanoethyl)ethanolamine, N,N-di-(2-cyanoethyl)ethanolamine, N-(2-cyanoethyl)diethanolamine and N-(2-cyanoethyl)propanolamine;

β-cyanoethylated amides such as those represented cyanoethylated acetamide and cyanoethylated propionamide; and, aromatic nitriles which may be used in the process include: benzyl cyanide, benzonitrile, isophthalonitrile and terephthalonitrile.

However, the preferred nitriles are the fatty nitriles having from 8–18 carbon atoms.

A wide variety of primary amines may be used in the reductive amination process. Representative amines which can be used in the reductive amination process are represented by the formula R'NH$_2$ where R' is lower alkyl having from ($C_1$ to $C_8$) carbons or aryl. Examples of candidate amines include primary amines such as monomethylamine, monoethylamine, monopropylamine, diamines such as ethylenediamine, propylenediamine, N-ethylethylenediamine, alkanolamines such as, ethanolamine, ether amines such as methoxypropylamine, methoxyethylamine, ethoxyethylamine, aryl amines such benzyl amine and cycloaliphatic amines such as cyclohexylamine. Preferred amines are the primary $C_{1-4}$ alkylamines, specifically methyl and ethyl amine.

Palladium is the heterogenous reductive amination catalytic metal of choice for the reductive amination reaction. Typically, the reductive amination catalyst is carried upon a heterogeneous support for ease of removal from the reaction medium. Representative supports include carbon, alumina, silica, kielsulghur, and the like. The heterogeneous catalytic metal component, palladium, is carried on the support in an amount usually ranging from about 2 to 20% by weight and preferably from 3–10% and most preferably from 4 to 6% by weight. Other metals such as ruthenium, rhodium, copper, and platinum offer little in the way of enhanced selectivity and reaction rate as compared to palladium.

The loading of heterogenous reductive amination catalyst, and particularly the palladium catalyst including support, in the process is the same as the loading level (Pd level of from 3–6 wt % based on the weight of Pd plus support) commonly used in prior art processes, e.g., from 0.1 wt % to 5.0 wt %, dry weight basis, based upon the nitrile feed. Preferred levels range from 1 wt % to 3 wt % of the supported palladium catalyst, dry weight basis, with respect to the nitrile feed.

The mole ratio of nitrile to amine employed in the process may be within a range of 1.5 to 2.5 moles nitrile per mole of primary amine. Obviously, to produce di(fattyalkyl) alkylamine in complete conversion there must be 2 moles nitrile per mole amine. It is possible to use less than 2 moles nitrile per mole amine but the reaction product will contain a mixture of mono and di(fattyalkyl)alkylamine. Normally, a slight excess of nitrile is used to insure complete reductive coupling to the di(fattyalkyl)alkylamine.

A key to effectiveness of the reductive amination process lies in the use of an effective amount of an acidic promoter. By effective amount it is meant that amount of an acidic promoter, preferably solid phase, to promote conversion to the di(fattyalkyl)alkylamine as compared to a non-promoted process. The preferred acidic promoters are ones having a pK of less than or equal to about 2 relative to water. For reasons of efficiency in processing, a solid phase acidic material is used as the promoting agent. When a solid phase acidic promoter is employed, not only must the promoter have the desired acidic pK, it should have a sufficiently large pore size, if it is in the form of a zeolite cage structure, to permit the reactants and product to enter and leaved the cage structure. For example, small pore size zeolites may not accommodate the large size of the di(fattyalkyl)nitrile even though they have the desired acidity.

Examples of acidic promoters include the hydrogen or H form of zeolites which is embraced by acidic montmorillonite, such as K-10 montmorillite, mordenite, X or Y zeolites, dealuminated mordenite and dealuminated X or Y zeolites which have high acidity values but also larger cage structures than the nondealuminated mordenites and zeolites from which they are derived. Other solid acids include sulfonated acidic ion exchange resins such as sulfonated styrene/divinyl benzene resins sold under the trademark Amberlyst®. Aluminosilicates, sulfated oxides such as sulfated zirconia or sulfated niobia, and cesium-promoted phosphotungstic acid also are examples of solid phase acidic promoters. Liquid phase acids may be used as a promoter but they are not easy to separate from the reaction medium. Examples include sulfuric acid, methane sulfonic acid and toluene sulfonic acid.

The level of promoter employed is that which is effective for promoting conversion to the di(fattyalkyl)alkylamine. Typically the acid will be provided to the reaction medium in an amount of from 0.1 to 3 and preferably from 1 to 2 grams per gram catalyst. Levels of solid acid phase promoters above about 3 grams per gram of catalyst, including support, do not offer significant advantages.

A class of polar solvents which are particularly suited for use in the reductive amination process are the lower $C_1$–$C_6$ alkanois and particularly methanol, isopropanol, butanol, and so forth. Tetrahydrofuran and a variety of ethers such as diethyl ether may be used. Typically, the solvent is added in a proportion of about 10 to 1000%, preferably 25 to 200% by weight of the nitrile to be added to the reaction medium. Amounts larger than 200% simply expand and exacerbate the recovery problem. Of the solvents, isopropanol is a preferred solvent as it is economic and also enhances the dissolution of hydrogen therein to maintain catalyst activity during the reductive amination process.

The reduction of the nitrile to the amine is carried out under a hydrogen pressure of from 50 to 2000 psig, typically from 400 to 600 psig, and at temperatures of from about 75 to 100° C., typically 100 to 160° C. Typical batch reaction times range from 15 to 600 minutes.

The following examples are provided to illustrate various embodiments of the invention and are not intended to restrict the scope thereof.

EXAMPLE 1

Control Reaction for Reductive Coupling of Cocoalkyl Nitrile With Methylamine (no added solid acid)

A 300 mL 316SS autoclave was charged with 0.98 gm (dry weight basis) of 5% Pd/C, followed by addition of a solution of 98.0 gm (0.50 mole) of commercial cocoalkyl nitrile in 45.0 gm (0.75 mole) of isopropanol. The autoclave was closed, purged with nitrogen and hydrogen, charged with 7.8 gm (0.25 mole) methylamine, and pressurized to ca 200 psig with hydrogen. The mixture was heated with stirring at 1500 rpm to 125° C. and pressurized with hydrogen to 450 psig. The reaction was maintained at this temperature; pressure was maintained at 450 psig via regulated hydrogen feed. After 5.0 hr, the mixture was cooled to room temperature, and the product removed from the reactor by filtration through an internal $0.5\mu$ sintered metal element. Analysis of the product by GC and GC-MS indicated 92% conversion of the nitrile; the product (feed-free basis) consisted of 70% di(cocoalkyl)methylamine, 29% (cocoalkyl) methylamine, and 1% cocoalkylamine.

EXAMPLE 2

Reductive Coupling of Cocoalkyl Nitrile with Methylamine (1.0 wt % added K 10 montmorillonite, based on weight of nitrile)

The procedure of Example 1 was repeated, with addition of 1.0 gm of K 10 montmorillonite, an acidic montmorillonite, after addition of the solution of cocoalkyl nitrile in isopropanol. After 6.0 hr, hydrogen uptake appeared to be complete. The reaction was cooled to room temperature, and the product isolated and analyzed as before. Conversion of the nitrile was 92%. The product (feed-free basis) consisted of 76% di(cocoalkyl) methylamine, 21% (cocoalkyl)methylamine, and 1% cocoalkylamine.

EXAMPLE 3

Reductive Coupling Of Cocoalkyl Nitrile With Methylamine (0.8 Equivalent Of Methylamine, Based On Nominal Equivalent Weight Of 196 For Cocoalkylnitrile)

The procedure of Example 1 was repeated, with addition of 6.2 gm (0.2 mole; 0.8 equivalent, based on nominal equivalent weight of 196 for cocoalkylnitrile) of methylamine. After 6.5 hr, the reaction was cooled to room temperature, and the product isolated and analyzed as before. Conversion of the nitrile was 99%. The product (feed-free basis) consisted of 93% di(cocoalkyl) methylamine, 5% (cocoalkyl)methylamine, 1% cocoalkylamine, and 1% di(cocoalkyl)amine.

EXAMPLE 4

Reductive Coupling of Cocoalkyl Nitrile with Methylamine (0.8 equivalent of methylamine, based on nominal equivalent weight of 196 for cocoalkylnitrile; 2.0 wt % added K 10 montmorillonite, based on weight of nitrile)

The procedure of Example 3 was repeated, with addition of 2.0 gm of K 10 montmorillonite. Rapid hydrogen uptake was observed. After 5.5 hr, the reaction was cooled to room temperature, and the product isolated and analyzed as before. Conversion of the nitrile was 97%. The product (feed-free basis) consisted of 96% di(cocoalkyl) methylamine, 2% (cocoalkyl)methylamine, <1% cocoalkylamine, and <1% di(cocoalkyl)amine.

EXAMPLE 5

Reductive Coupling Of Cocoalkyl Nitrile With Methylamine (0.8 Equivalent Of Methylamine, Based On Nominal Equivalent Weight Of 196 For Cocoalkylnitrile 2.0 Wt % Added HY Zeolite, Based On Weight Of Nitrile)

The procedure of Example 4 was repeated, with addition of 2.0 gm of HY zeolite. After 7 hr, the reaction was cooled to room temperature, and the product isolated and analyzed as before. Conversion of the nitrile was >99%. The product (feed-free basis) consisted of 95% di(cocoalkyl)methylamine, 1% (cocoalkyl)methylamine, 1% cocoalkylamine, and 3% di(cocoalkyl)amine.

EXAMPLE 6

Reductive Coupling Of Cocoalkyl Nitrile With Methylamine (0.8 Equivalent Of Methylamine, Based On Nominal Equivalent Weight Of 196 For Cocoalkylnitrile; 2.0 Wt % Added HZSM-5 Zeolite, Based On Weight Of Nitrile)

The procedure of Example 5 was repeated, with addition of 2.0 gm of HZSM-5 zeolite. After 6 hr, the reaction was cooled to room temperature, and the product isolated and analyzed as before. Conversion of the nitrile was 98%. The product (feed-free basis) consisted of 92% di(cocoalkyl)methylamine, 7% (cocoalkyl)methylamine, 1% cocoalkylamine, and 1% di(cocoalkyl)amine.

EXAMPLE 7

Reductive Coupling Of Cocoalkyl Nitrile With (0.8 Equivalent Of Methylamine Based On Nominal Equivalent Weight Of 196 For Cocoalkylnitrile; 2.0 Wt % Added γ-Alumina, Based On Weight Of Nitrile)

The procedure of Example 5 was repeated, with addition of 2.0 gm of γ-alumina. After 6.5 hr, the reaction was cooled to room temperature, and the product isolated and analyzed as before. Conversion of the nitrile was 94%. The product (feed-free basis) consisted of 84% di(cocoalkyl)methylamine, 15% (cocoalkyl)methylamine, and 1% cocoalkylamine.

COMMENTS ON EXAMPLES 1–7

Example 2 shows the result of inclusion of an effective solid acid, K 10 montmorillonite (a relatively high surface area acidic clay), in the reaction of (0.25 moles) MMA with a 0.5 mole sample of commercial cocoalkyl nitrile (a mixture of predominantly linear $C_8$, $C_{10}$, $C_{12}$, $C_{14}$, $C_{16}$ and $C_{18}$ saturated nitriles) in the appropriate stoichiometry (cf eqn 1), assuming the producer's cited average equivalent weight of 194. Inclusion of K 10 montmorillonite provides a modest improvement in selectivity to di(cocoalkyl)methylamine and lower selectivity to the intermediate (cocoalkyl)methylamine over the Example 1 control and thus shows its use in an effective amount. (The relatively high selectivity to cocoalkylmethylamine coupled with the absence of unreacted nitrile or large amounts of cocoalkylamine or di(cocoalkyl)amine, suggested that the true equivalent weight of this sample of cocoalkyl nitrile was higher than the cited value.)

Example 3 shows the result of reaction with less MMA (stoichiometrically identical to Example 2 assuming a higher equivalent weight for the cocoalkyl nitrile). In this example, selectivity to the desired di(cocoalkyl)methylamine was significantly higher, and less of the intermediate was isolated.

Examples 4 and 5 demonstrate the effectiveness of both K 10 and HY zeolite (an acidic large pore zeolite) in improving the selectivity to di(cocoalikyl)methylamine in contrast to the Example 1 control.

Example 6 demonstrates the relative ineffectiveness of HZSM-5 zeolite (a medium pore zeolite, 5.3–5.6 A°). Preferably, then an acceptable zeolite should have a pore size greater than that of ZSM -5.

Example 7 demonstrates the effect of γ-alumina (a weakly acidic solid, a pK greater than 2) as compared to Examples 2–5 acidic promoters in improving selectivity to di(cocoalkyl)methylamine.

EXAMPLE 8

Reductive Coupling Of A Second Lot Of Cocoalkyl Nitrile With Methylamine (No Added Solid Acid)

The procedure of Example 1 was repeated with a second lot of commercial cocoalkyl nitrile. After 5.5 hr, the mixture was cooled to room temperature, and the product removed from the reactor by filtration through an internal $0.5\mu$ sintered metal element. Analysis of the product by GC and GC-MS indicated >99% conversion of the nitrile; the product (feed-free basis) consisted of 88% di(cocoalkyl)methylamine, 11% (cocoalkyl)methylamine, and 1% di(cocoalkyl)amine.

EXAMPLE 9

Reductive Coupling of a Second Lot of Cocoalkyl Nitrile with Methylamine (0.88 equivalent of methylamine, based on nominal equivalent weight of 196 for cocoalkylnitrile) (No Solid Acid Promoter)

The procedure of Example 8 was repeated, with addition of 7.0 gm (0.22 mole or 0.88 equivalent, based on nominal equivalent weight of 196 for cocoalkylnitrile) of methylamine. After 6.0 hr. the reaction was cooled to room temperature, and the product isolated and analyzed as before. Conversion of the nitrile was 98%. The product (feed-free basis) consisted of 93% di(cocoalkyl)methylamine, 5% (cocoalkyl)methylamine, 1% cocoalkylamine, and 1% di(cocoalkyl)amine.

EXAMPLE 10

Reductive Coupling Of A Second Lot Of Cocoalkyl Nitrile With Methylamine (0.88 Equivalent Of Methylamine, Based On Nominal Equivalent Weight Of 196 For Cocoalkylnitrile; 2.0 Wt % added K 10 montmorillonite, based on weight of nitrile)

The procedure of Example 9 was repeated, with addition of 2.0 gm of K 10 montmorillonite after the solution of cocoalkyl nitrile in isopropanol. After 5.5 hr, hydrogen uptake appeared to be complete. The reaction was cooled to room temperature, and the product isolated and analyzed as before. Conversion of the nitrile was >99%. The product (feed-free basis) consisted of 97% di(cocoalkyl)methylamine, <1% (cocoalkyl)methylamine, 1% cocoalkylamine, and 2% di(cocoalkyl)amine.

EXAMPLE 11

Reductive Coupling of a Second Lot of Cocoalkyl Nitrile with Methylamine (0.88 equivalent of methylamine, based on nominal equivalent weight of 196 for cocoalkylnitrile; 2.0 wt % added Nation®, based on weight of nitrile)

The procedure of Example 9 was repeated, with addition of 2.0 gm of Nafion® after the solution of cocoalkyl nitrile in isopropanol. After 6.5 hr, the reaction was cooled to room temperature, and the product isolated and analyzed as before. Conversion of the nitrile was 98%. The product (feed-free basis) consisted of 83% di(cocoalkyl)methylamine, 15% (cocoalkyl)methylamine, 1% cocoalkylamine, and 1% di(cocoalkyl)amine.

COMMENTS ON EXAMPLES 8–11

Example 8 demonstrates reactivity of MMA with a second commercial sample of cocoalkyl nitrile in the appropriate stoichiometry again assuming the producer's cited equivalent weight of 196. The lower selectivity to di(cocoalkyl)methylamine and formation of a significant amount of (cocoalkyl)methylamine relative to Example 10 again indicates an excess of MMA, although not to the same extent as in Example 1 control.

Example 9 shows the improved selectivity through the use of less MMA and thereby increasing the molar ratio of fatty nitrile to MMA. The use of K 10 to further improve selectivity to di(cocoalkyl)methylamine is shown by Example 10, while Example 11 shows that Nafion®, an acidic gel ion exchange resin, is ineffective. It is believed that the gel structure of the Nafion promoter does not permit easy access to the acidic sites by either reactant.

EXAMPLE 12

Control Reaction For The Reductive Coupling Of Tallow Nitrile With Methylamine (No Added Solid Acid)

The procedure of the Example 1 control was repeated with commercial tallow nitrile. After 5.5 hr, the mixture was cooled to room temperature, and the product removed from the reactor by filtration through an internal $0.5\mu$ sintered metal element. Analysis of the product by GC and GC-MS indicated 96% conversion of the nitrile; the product (feed-free basis) consisted of 72% di(tallow)methylamine, 27% (tallow)methylamine, <1% tallow amine and <1% di(tallow)amine.

CONTROL EXAMPLE 13

Control Reaction For Reductive Coupling Of Tallow Nitrile With Methylamine (0.71 Equivalent Of Methylamine, Based On Nominal Equivalent Weight Of 258 For Tallow Nitrile) (No Added Acidic Promoter)

The procedure of Example 12 was repeated, with addition of 5.5 gm (0.177 mole; 0.71 equivalent, based on nominal equivalent weight of 258 for tallow nitrile) of methylamine. After 6.5 hr, the reaction was cooled to room temperature, and the product isolated and analyzed as before. Conversion of the nitrile was 97%. The product (feed-free basis) consisted of 82% di(tallow)methylamine, 16% (tallow)methylamine, 1% tallow amine, and 1% di(tallow)amine.

EXAMPLE 14

Reductive Coupling Of Tallow Nitrile With Methylamine (0.71 Equivalent Of Methylamine, Based On Nominal Equivalent Weight Of 258 For Tallow Nitrile; 2.0 Wt % Added K 10 Montmorillonite, Based On Weight Of Nitrile)

The procedure of Example 13 was repeated, with addition of 2.6 gm of K 10 montmorillonite. After 7.0 hr, the reaction was cooled to room temperature, and the product isolated and analyzed as before. Conversion of the nitrile was 96%. The product (feed-free basis) consisted of 86% di(tallow)methylamine, 12% (tallow)methylamine, 1% tallow amine, and 1% di(tallow)amine.

COMMENTS ON EXAMPLES 12–14

Examples 12–14 demonstrate application of this invention to a commercial sample of tallow nitrile. Example 12 shows the selectivity that is obtained upon reaction of MMA with tallow nitrile at the appropriate stoichiometry, assuming the producer's cited equivalent weight of 258. Selectivity to the desired di(tallow)methylamine is relatively low, while a significant concentration of (tallow)methylamine is formed. As before, these results, coupled with the absence of significant amounts of products derived solely from tallow nitrile, indicate the presence of excess MMA.

Example 13 shows the improved selectivity that results upon use of less MMA.

Example 14 shows that with added K 10 an additional modest improvement in selectivity to the desired product was obtained as compared to Control Example 13.

CONTROL EXAMPLE 15

Reductive Coupling of a Second Lot of Tallow Nitrile With Methylamine (No Added Solid Acid)

The procedure of the Example 12 control was repeated with a second lot of commercial tallow nitrile. After 7.0 hr, the mixture was cooled to room temperature, and the product removed from the reactor by filtration through an internal $0.5\mu$ sintered metal element. Analysis of the product by GC and GC-MS indicated 98% conversion of the nitrile; the product (feed-free basis) consisted of 60% di(tallow)methylamine, 32% (tallow)methylamine, 1% tallow amine and 3% di(tallow)amine.

EXAMPLE 16

Reductive Coupling Of A Second Lot Of Tallow Nitrile With Methylamine (0.61 Equivalent Of Methylamine, Based On Nominal Average Equivalent Weight Of 256 For Tallow Nitrile) No Added Acidic Promoter The procedure of Example 15 was repeated, with addition of 4.7 gm (0.152 mole; 0.61 equivalent, based on nominal average equivalent weight of 256 for tallow nitrile) of methylamine. After 7.0 hr, the reaction was cooled to room temperature, and the product isolated and analyzed as before. Conversion of the nitrile was 97%. The product (feed-free basis) consisted of 89% di(tallow)methylamine, 5% (tallow)methylamine, 1% tallow amine, and 5% di(tallow)amine.

EXAMPLE 17

Reductive Coupling Of A Second Lot Of Tallow Nitrile With Methylamine (0.61 Equivalent Of Methylamine, Based On Nominal Average Equivalent Weight Of 256 For Tallow Nitrile; 1.6 Wt % Added HY Zeolite, Based On Weight Of Nitrile)

The procedure of Example 16 was repeated, with addition of 2.0 gm of HY zeolite. After 6.5 hr, the reaction was cooled to room temperature, and the product isolated and analyzed as before. Conversion of the nitrile was 99%. The product (feed-free basis) consisted of 92% di(tallow)methylamine, 1% (tallow)methylamine, 2% tallow amine, and 5% di(tallow)amine.

EXAMPLE 18

Reductive Coupling Of A Second Lot Of Tallow Nitrile With Methylamine (0.61 Equivalent Of Methylamine, Based On Nominal Average Equivalent Weight Of 256 For Tallow Nitrile; 1.6 Wt % Added NaY Zeolite, Based On Weight Of Nitrile)

The procedure of Example 16 was repeated, with addition of 2.0 gm of NaY zeolite. After 7.0 hr, the reaction was cooled to room temperature, and the product isolated and analyzed as before. Conversion of the nitrile was 98%. The product (feed-free basis) consisted of 87% di(tallow)methylamine, 5% (tallow)methylamine, 1% tallow amine, and 7% di(tallow)amine.

COMMENTS ON EXAMPLE 15–18

Examples 15–18 demonstrate application of this invention to a second lot of commercial tallow nitrile. Example 15 shows the selectivity that is obtained upon reaction of MMA with tallow nitrile at the appropriate stoichiometry, assuming the producer's cited average equivalent weight of 256. Selectivity to the desired di(tallow)methylamine is low, while a significant concentration of (tallow)methylamine is formed. As before, these results, coupled with the absence of significant amounts of products derived solely from tallow nitrile, indicate the presence of excess MMA.

Example 16 shows the improved selectivity that results upon use of less MMA, i.e., using a higher mole ratio of nitrile to amine. The use of HY zeolite to further improve selectivity to di(tallow)methylamine is shown by Example 17, while Example 18 shows that NaY zeolite, a neutralized form of HY zeolite, is much less effective. Use of Alkali Metal Hydroxide

CONTROL EXAMPLE 1

This space is reserved for the Example 1 control, and is repeated here for ease of discussion.

COMPARATIVE EXAMPLE 2

Reductive Coupling Of Cocoalkyl Nitrile With Methylamine (0.50 Wt % Added Lithium, Based On Dry Weight Of Catalyst, As Lithium Hydroxide Monohydrate)

The procedure of Example 1 was repeated, with addition of 0.0297 gm ($7.08 \times 10^{-4}$ mole) of lithium hydroxide monohydrate in 1.0 mL of water after the solution of cocoalkyl nitrile in isopropanol. After 5.0 hr, the reaction was cooled to room temperature, and the product isolated and analyzed as before. Conversion of the nitrile was 88%. The product (feed-free basis) consisted of 65% di(cocoalkyl)methylamine, 32% (cocoalkyl)methylamine, 1% cocoalkylamine, and 1% di(cocoalkyl)amine.

COMPARATIVE EXAMPLE 3

Reductive Coupling Of Cocoalkyl Nitrile With Methylamine (0.75 Wt % Added Lithium, Based On Dry Weight Of Catalyst, As Lithium Hydroxide Monohydrate)

The procedure of the Example 1 control was repeated, with addition of 0.0445 gm ($1.06 \times 10^{-3}$ mole) of lithium hydroxide monohydrate in 1.0 mL of water after the solution of cocoalkyl nitrile in isopropanol. After 5.0 hr, the reaction was cooled to room temperature, and the product isolated and analyzed as before. Conversion of the nitrile was 76%. The product (feed-free basis) consisted of 51% di(cocoalkyl)methylamine, 49% (cocoalkyl)methylamine, <1% cocoalkylamine, and <1% di(cocoalkyl)amine.

COMPARATIVE EXAMPLE 4

Reductive Coupling Of Cocoalkyl Nitrile With Methylamine (1.00 Wt % Added Lithium, Based On Dry Weight Of Catalyst, As Lithium Hydroxide Monohydrate)

The procedure of the Example 1 control was repeated at 150° C. and 800 psig, with addition of 0.0594 gm ($1.42 \times 1^{-3}$ mole) of lithium hydroxide monohydrate in 1.0 mL of water after the solution of cocoalkyl nitrile in isopropanol. After 7.5 hr, the reaction was cooled to room temperature, and the product isolated and analyzed as before. Conversion of the nitrile was 83%. The product (feed-free basis) consisted of 40% di(cocoalkyl)methylamine, 56% (cocoalkyl)methylamine, 1% cocoalkylamine, and 3% di(cocoalkyl)amine.

COMMENTS ON COMPARATIVE EXAMPLES 1–4

Recall the Example 1 control shows that, in the absence of lithium hydroxide (2:1 mole ratio cocoalkyl nitrile:MMA; isopropanol solvent; 125° C.) with a relatively low catalyst loading (1.0 wt %, dry weight basis, based on nitrile), di(cocoalkyl)methylamine was produced in moderate selectivity (70%); the intermediate mono(cocoalkyl)methylamine was the major coproduct.

LiOH comparisons

Comparative Example 2 shows the effect of the inclusion of 0.5 wt % lithium (as lithium hydroxide monohydrate, based on dry weight of the catalyst) on the product slate.

Comparative Example 3 shows the effect on conversion or selectivity with 0.75 wt % lithium hydroxide.

Example 4 shows the effect of 1 wt % LiOH promoter.

Comparative Examples 3 and 4 show successively lower selectivities to di(cocoalkyl)methylamine (54%, 40% respectively), while the intermediate mono(cocoalkyl)methylamine became the predominant product (44%, 56% respectively). These experiments show that lithium hydroxide modification of the palladium/carbon catalyst does not promote selective formation of di(cocoalkyl)methylamine from cocoalkyl nitrile.

What is claimed is:

1. In a process for the catalytic reductive amination of fatty nitriles which comprises reacting a nitrile with a primary amine in the presence of a heterogeneous metal reductive amination catalyst under hydrogen pressure and under conditions for effecting conversion of the nitrile group to the tertiary amine, the improvement which resides in effecting the reductive amination in the presence of an effective amount of an acidic promoter.

2. The process of claim 1 wherein the acidic promoter is a solid phase acidic promoter having a pK of less than or equal to about 2 relative to water.

3. The process of claim 2 wherein the solid phase acidic promoter is present in an amount from 0.1 to 3 grams per gram of catalyst.

4. The process of claim 3 wherein the solid phase acidic promoter is selected from the group consisting of acidic montmorillonite, mordenite, the hydrogen form of X or Y zeolites, dealuminated mordenite, dealuminated X or Y zeolite, sulfonated ion exchange resins, aluminosilicates, sulfated oxides, sulfated zirconia or sulfated niobia, and cesium-promoted phosphotungstic acid.

5. The process of claim 4 wherein the primary amine that is reacted with the nitrile is represented by the formula $R'NH_2$ where R' is lower aliphatic having from 1–8 carbon atoms.

6. The process of claim 5 wherein the nitrile is an aliphatic nitrile having from 2–30 carbon atoms.

7. The process of claim 6 wherein the amine has from 1–4 carbon atoms.

8. The process of claim 7 wherein the nitrile is a fatty nitrile having from 8–20 carbon atoms.

9. The process of claim 8 wherein the heterogenous reductive amination catalyst is palladium carried on a support and the supported palladium catalyst is employed in an amount of from 0.1 to 5% with respect to the nitrile feed.

10. The process of claim 9 wherein the fatty nitrile is selected from the group consisting of lauronitrile, stearonitrile, cocoalkyl nitrile, oleonitrile, and tallow fatty acid nitrile.

11. The process of claim 10 wherein the primary amine is ethylamine or methylamine.

12. The process of claim 11 wherein the acidic promoter is selected from the group consisting of the hydrogen form of X or Y zeolite, dealuminated mordenite, dealuminated X or Y zeolite, K 10 montmorillonite and a sulfonated ion exchange resin.

13. The process of claim 6 wherein the aliphatic nitrile is a $\mu$-aminonitrile or a $\mu$alkoxynitrile.

14. The process of claim 13 wherein the aliphatic nitrile is a β-aminonitrile selected from the group consisting of: β-aminopropionitrile, di-(2-cyanoethyl)amine, N-methyl-β-aminopropionitrile, N,N-dimethyl-β-aminopropionitrile, N-ethyl-β-amino-propionitrile, N,N-diethyl-β-aminopropionitrile, mono-(2-cyanoethyl)methylamine; di-(2-cyanoethyl)methylamine, N-(2-cyanoethyl) ethanolamine, N,N-di-(2-cyano-ethyl)ethanolamine, N-(2-cyanoethyl)diethanolamine,N-(2-cyanoethyl) propanolamine, N-(2-cyanoethyl)stearylamine, N-(2-cyanoethyl)cocoalkyamine, N-(2-cyano-ethyl)oleylamine, or N-(2-cyanoethyl)cocoalkylamine.

15. The process of claim 6 wherein the aliphatic nitrile is an alkoxy nitrile represented by the formula:

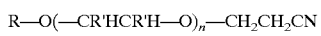

where R=$C_1$ to $C_{30}$alkyl radical, R'=H or $C_1$ to $C_8$ alkyl radical and n=1 to 30.

16. The process of claim 15 wherein the alkoxy nitrile is selected from the group consisting of methoxypropionitrile, bis-cyanoethytether, mono-(2-cyanoethyl)ethylene glycol; bis-(2-cyanoethyl)ethyleneglycol, mono-(2-cyanoethyl) diethyleneglycol; bis-(2-cyanoethyl)diethyleneglycol; bis(2-cyanoethyl)tetramethyleneglyrol, cyanoethyl stearyl ether, cyanoethyl oleyl ether, cyanoethyl cocoalkyl ether, or cyanoethyl lauryl ether.

17. The process of claim 5 wherein the nitrile is a cyanoethylated amide represented by the formula; $RCON(CH_2CH_2CN)_n$ where R is H or a $C_{1-18}$ alkyl radical and n is 1 or 2.

18. The process of claim 17 wherein the cyanoethylated amide is selected from the group consisting of cyanoethylated acetamide and cyanoethylated propionamide.

* * * * *

UNITED STATES PATENT AND TRADEMARK OFFICE
CERTIFICATE OF CORRECTION

PATENT NO.    : 6,399,830 B1
DATED         : June 4, 2002
INVENTOR(S)   : John Nelson Armor, Michael Edward Ford and William Eamon Carroll It is certified that error appears in the above-identified patent and that said Letters Patent is hereby corrected as shown below:

Column 13,
Line 31, delete "µ-aminonitrile" and substitute therefor -- β-aminonitrile --; and delete "µalkoxynitrile" and substitute therefore -- β-alkoxynitrile --

Signed and Sealed this

First Day of October, 2002

Attest:

Attesting Officer

JAMES E. ROGAN
Director of the United States Patent and Trademark Office